US006235497B1

(12) United States Patent
Bejanin et al.

(10) Patent No.: US 6,235,497 B1
(45) Date of Patent: *May 22, 2001

(54) RECOMBINANT EXPRESSION OF THE RAT VESICULAR ACETYLCHOLINE TRANSPORTER

(75) Inventors: Stéphane Bejanin, Paris; Sylvie Berrard, Rueil-Malmaison; Riccardo Cervini, Saint-Cloud; Jacques Mallet, Paris, all of (FR)

(73) Assignee: Rhone-Poulenc Rorer S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/793,044

(22) PCT Filed: Aug. 10, 1995

(86) PCT No.: PCT/FR95/01073

§ 371 Date: Apr. 21, 1997

§ 102(e) Date: Apr. 21, 1997

(87) PCT Pub. No.: WO96/05301

PCT Pub. Date: Feb. 22, 1996

(30) Foreign Application Priority Data

Aug. 16, 1994 (FR) .................................................. 94 10044

(51) Int. Cl.⁷ ........................... C12N 15/12; C12N 15/63; C12N 15/86

(52) U.S. Cl. .................... 435/69.1; 435/320.1; 536/23.1; 536/23.5; 536/24.1

(58) Field of Search ................................. 424/93.1, 93.2; 514/44; 536/23.1, 23.5, 24.1; 435/91.4, 320.1, 69.1; 935/9, 32

(56) References Cited

PUBLICATIONS

Benjanin et al., "A unique gene organization for two cholinergic markers, choline acetyltransferase and a putative vesicular transporter of acetylcholine", J. Biol. Chem. 269(35):21944–21947.*
Orkin et al., "Report and recommendations of the panelto assess the NIH investment in research on gene therapy", issued by the U.S. National Institutes of Health, Dec. 1995.*
Ngo et al., "Computational complexity, protein structure prediction, and the Levinthal paradox", in 'The Protein Folfing Problem and Tertiary Structure Prediction', Merz et al. (eds.), Birkhauser Boston, Boston, MA, pp. 433 and 492–495, 1994.*
Kaufman, "Vectors used ofr expression in mammalian cells", Meth. Enzymol. 185:487–511, 1990.*
Bonner, T.I., "Rattus norvegicus vesicular acetylcholine transporter mRNA, complete cds." (direct submission), GenBank, U.S. National Library of Medicine, Accession No. UO9211, accessed by PTO Jan. 20, 1998, Aug. 4, 1994.*
Mallet, J.J.M. GenBank Acc. X80395, Locus–RRRVAT, Aug. 1, 1994.
Bejanin et al., Promoter Elements of the Rat Choline Acetyltransferase Gene Allowing Nerve Growth Factor Inducibility in Transfected Primary Cultured Cells, J. Neurochemistry, 58(4), 1580–1583, (1992).
Levrero et al., Defective and Nondefective Adenovirus Vectors for Expressing Foreign Genes In Vitro and In Vivo, Gene, 101, 195–202, (1991).
Kengaku et al., Multiple mRNA Species of Choline Acetyltransferase from Rat Spinal Cord, Molecular Brain Research, 18, 71–76, (1993).
Varoqui et al., Cloning and Expression of the Vesicular Acetylcholine Transporter, Cell Biology International, 18(5), 502, (1994).
Alfonso et al., The Caenorhabditis Elegans UNC–17 Gene: A Putative Vesicular Acetylcholine Transporter, Science, 261, 617–619, (1993).
Bejanin et al., A Unique Gene Organization for Two Cholinergic Markers, Choline Acetyltransferase and a Putative Vesicular Transporter of Acetylcholine, Journal of Biological Chemistry, 269, 0, 1–4, (1994).
Erickson et al., Functional Identification of a Vesicular Acetylcholine Transporter and Its Expression from a "Cholinergic" Gene Locus, Journal of Biological Chemistry, 269, 35, 21929–21932, (1994).
Roghani et al., Molecular Cloning of a Putative Vesicular Transporter for Acetylcholine, Pro. Natl. Acad. Sci., USA, 91, 10620–10624, (1994).
Erickson et al., Identification of the Mammalian Vesicular Acetylcholine Transporter and Its Expression From A Cholinergic Gene Locus, J. Neurochem. 63, supp.1, (1994).
Misawa et al., Coordinante Expression of Vesicular Acetylcholine Transporter and Choline Acetyltransferase in Sympathetic Superior Cervical Neurones, Neuro Report, 6, 965–968, (1995).
Berrard et al., Coregulation of Two Embedded Gene Products, Choline Acetyltransferase and the Vesicular Acetylcholine Transporter, Journal of Neurochemistry, 65(2), 939–942, (1995).
Usdin et al., Molecular Biology of the Vesicular ACh Transporter, Trends in Neurosciences, 18(5), 218–224, (1995).

* cited by examiner

Primary Examiner—Scott D. Priebe
(74) Attorney, Agent, or Firm—Finnegan, Henderson, Farabow, Garrett & Dunner, L.L.P.

(57) ABSTRACT

A nucleic sequence coding for a protein involved in the vesicular transport of acetylcholine, the corresponding protein and the promoter sequences implicated in expressing said protein are disclosed. The invention also discloses expression vectors containing said sequence and the therapeutic use of said sequence or said vectors.

6 Claims, 3 Drawing Sheets

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 3925 base pairs
      (B) TYPE: nucleic acid
      (C) STRANDEDNESS: single
      (D) TOPOLOGY: linear    (ii) MOLECULE TYPE: cDNA    (xi) SEQUENCE DESCRIPTION: SEQ ID NO: 1:

```
AAGCTTCCAA GCCACTTGTG AGCCCACTCA GGGTTTGGAG GCGGACGGGG TGGGGGTGGG      60

GTGGGGAAAT GCAGAAAAGT GGGCGGAGGC TCTCAAGAGC CTAGGGAGGA TAAGGTCTGG     120

AAAGAAGAGG ACCTGGGAGG AGTTAGATTG AGGAGTGGGA GAGTAGAAGG GGAGGGAAAT     180

AGGCGGGGCT GGAGGCCGGG GAGACCCGCG CACCGAAAAG CCCAAAGGGA GAGTCCAGGC     240

AGGGGGAGGT CAAAAAGGGT TAGCGTTGAC ATCCAGGACC CTGGGTGCAG AGAAAGACTC     300

CTCCTCTCAG TCCTCATACC CTCATAGTTC AGAATTAGCT GCCAAGACTT TCTGCCTAAG     360

GGCGGTGGGT CGGAACCAGA GCCTGAAGGC TCTGTACCTC CCCCCTCCCT TCCCGGAGGA     420

GGGGATGGGA CGGGCTGGGG GCGGGATTGA GGAAGGGGGT TGCGTGCGCT GTGCCTCTGG     480

GTCCGGGCTG CGCGTTCCAG CTGCGAGAAC AGATGGAGGC AGCGCGGCTC ACCTCGGGGG     540

CTCCGTGCCC GCTGTGCGCC GAAGTCCAGG CTGAGGAGGA GGTCTAGAGC CCCCGGCTCT     600

CCCGTCTCCC ACCAGGCTGC GGGGAACTGG CTGCCGCACC CCTCCTCCAA GTGGGGGTAG     660
```

-continued

| | | |
|---|---|---|
| AACGGAGTCT CACCCCCATA GGTCCCAGAA CTAAGGGGAA CATAGGGCCG GTTCCTCCCA | 720 |
| CTGCTCAGCC ATCCCCAGGG GCTTGTCTAG GACTATAGCT CTCCAAATCC CCCTTCCCCT | 780 |
| GGCTTCCATC CTGGGCGCAT CTCAGAAGCG GACCCCTGCC CGGACGCGCC CCGCCCCCGG | 840 |
| CCCCCGCCCC GACGACGTCC TATTAGCATG AGCGACGCCA GTGGCCGGGG CACCACTCGG | 900 |
| GGGCCGAGAC TCACCGCGTC ATAGCCCCAA GTGGAGGGAG AAAGAAAAAA AAAGAGGCGG | 960 |
| CGGTGGAGGA AGAGGCAAGA GCGGACGGGC GGGGAGGGCT GGAGAGACGG CGGGCGGCGG | 1020 |
| CAGCATGCCC CTGGGCGGGT GCACACGGCC TCTCTGCACC GCAGGGGCTG CTTCTGCTCT | 1080 |
| CTCTGGGCAC CACGCGTCCA GTCTCCCGCC TCAGCCCCTC GGCTTGCCGG CCTTTGCGGT | 1140 |
| TGCGCTCGAA ACATCGTCCA CTGGTCCCCG AAGCATCTAA GAGCAGCGGC GCCGCGCGGG | 1200 |
| ACAATCCTTG CTTTTTTCTG AGCTCGGGGA TATGAGCCCC ACAGCCACCT GAAGCGCAGG | 1260 |
| GGGCGCTACG GCTAGGACCG CGCCCCCGAA GTACCTTATC CTAGCCTCTG CACTGCGGGA | 1320 |
| CGCCGACACC CGACTCCGGT GGAGGCATCT TAGGGAAAGC AGCCGGTAGG GGCATGGAAC | 1380 |
| CCACCGCGCC AACCGGTCAG GCCCGGGCGG CGGCCACCAA ACTGTCGGAA GCGGTGGGAG | 1440 |
| CCGCGCTACA AGAGCCCCAG AGGCAGCGGC GCCTGGTGCT GGTCATCGTG TGCGTTGCAC | 1500 |
| TGTTACTGGA CAACATGTTG TACATGGTCA TCGTGCCCAT TGTTCCCGAC TATATCGCCC | 1560 |
| ACATGCGCGG GGGCAGCGAG GGCCCGACCC TGGTCTCTGA GGTGTGGGAA CCCACTCTGC | 1620 |
| CGCCGCCCAC TCTGGCTAAT GCCAGTGCCT ACTTGGCCAA CACGTCGGCG TCCCCGACGG | 1680 |
| CTGCCGGGTC GGCTCGGTCA ATCCTGCGAC CTCGCTACCC CACAGAAAGC GAAGATGTGA | 1740 |
| AGATAGGTGT GCTGTTTGCC TCCAAGGCTA TCCTGCAGCT TCTGGTGAAC CCCTTAAGCG | 1800 |
| GGCCTTTCAT TGATCGCATG AGCTACGACG TGCCGCTGCT TATAGGCCTG GGCGTCATGT | 1860 |
| TCGCCTCCAC AGTCATGTTT GCCTTTGCAG AAGACTATGC CACGCTCTTC GCTGCGCGCA | 1920 |
| GTCTACAAGG CCTGGGCTCG GCCTTCGCGG ACACGTCTGG CATTGCCATG ATCGCCGACA | 1980 |
| AGTATCCCGA GGAGCCTGAG CGCAGTCGTG CCCTGGGCGT GGCGCTAGCC TTTATTAGCT | 2040 |
| TTGGAAGCCT AGTGGCGCCA CCGTTTGGGG GCATCCTCTA CGAGTTCGCG GGCAAGCGTG | 2100 |
| TACCCTTTCT AGTGCTCGCC GCTGTGTCCC TTTTCGACGC GCTCCTGCTC CTGGCGGTGG | 2160 |
| CTAAGCCCTT CTCGGCTGCG GCTCGGGCGC GAGCCAACCT GCCGGTGGGC ACACCTATCC | 2220 |
| ATCGCCTCAT GCTAGACCCT TACATCGCTG TGGTAGCCGG CGCGCTCACC ACTTGTAACA | 2280 |
| TTCCCCTTGC GTTCCTCGAG CCCACCATAG CCACGTGGAT GAAGCACACA ATGGCCGCAT | 2340 |
| CCGAGTGGGA GATGGGCATG GTTTGGCTGC CGGCTTTCGT GCCACACGTG TTAGGCGTCT | 2400 |
| ACCTCACCGT GCGCCTGGCG GCGCGTTATC ACACCTGCA GTGGCTGTAC GGCGCTCTCG | 2460 |
| GGCTAGCGGT AATTGGAGTG AGCTCTTGCG TCGTACCTGC CTGTCGCTCA TTCGCGCCGT | 2520 |
| TAGTGGTCTC GCTCTGCGGA CTCTGCTTCG GCATCGCGTT AGTGGACACA GCGCTCCTAC | 2580 |
| CCACGCTCGC CTTTCTGGTG GACGTGCGCC ACGTATCCGT CTATGGCAGT GTCTATGCCA | 2640 |
| TAGCTGACAT CTCCTATTCT GTGGCCTACG CGCTCGGGCC CATAGTGGCA GGCCACATCG | 2700 |
| TTCACTCTCT TGGCTTTGAG CAGCTCAGCC TGGGCATGGG CCTGGCCAAC CTGCTCTACG | 2760 |
| CACCAGTCCT TCTTCTTTTG CGCAATGTAG GCCTCCTTAC ACGCTCGCGT TCGGAGCGCG | 2820 |
| ATGTGTTGCT TGATGAACCG CCGCAGGGTC TGTACGACGC GGTGCGCCTG CGTGAGGTGC | 2880 |
| AGGGCAAGGA TGGCGGCGAA CCTTGTAGCC CACCTGGCCC TTTTGACGGG TGCGAGGACG | 2940 |
| ACTACAACTA TTACTCCCGC AGCTAGCAGA CCCGCTTCTC CTCCAGGCCA CCTACCCGCC | 3000 |
| CCATTTAGGT CAAGATGGTC ATTCTGCAAG AGCACTGTCC AACTTTGGCT TGGGGCCCAC | 3060 |

-continued

```
CTCCTCTAAT GAATACCCTA GCCCCTCGCC CGTCCTGAAT TCCTTTGCTG GAATCCCTTC        3120

TCCATGACCC CTCCCAGTCT AGGCCCCTCC CAAACACACT CGTATTCATT GGGGAAATGG        3180

AGCAGGGAGG CAGAAGAAGC TGTTGGGCTC TTGGCAGAGG TGAAGAGGTG TGCGGGTGAT        3240

CGCCAATCAC CTACTGAGAG CCCCCAAATA GAGTCATGCA TCTGTTTGTC CTTCCTGCGG        3300

ATCTTTCCAG TGCCAAACTT GGTCTCTGCA CTCCGGTGCC TCCGGCCTGA ATTAATAAAC        3360

CATATCTATC TGAGGAGGCC GAGTCTCTTT ACTGATGAGG GGTGGGTGGT GTGACACAAG        3420

ACCTAAGCAC AGAGAAGGCT GCCTGGGTTT CACAGGTTCA GTCCAGACCT GAGGAGGAGG        3480

GGAAGCCTGA AGCGTCTTTG CTGCCTGGTA AAAGAACCCA AAGGAGGGCT CTCCCCCATG        3540

GATATTCAGA ACACACACAC ACACACACAC ACTCACACAC ACACACACAC ACACACACAC        3600

ACACACGAAC GATAGACAGA CAGACAGACA GACAGACAGA CAGACAGTCT CTCCCTTCCA        3660

AGTCCAGTGT AGCACCTGGA GGTTCCACCC GAGGGAGCCT GAGGATCGC CTGGCCTTGG         3720

AGGATAGCTG GCACCAGGAA TTTTGGGTGC CAGGACTGGG CTTTCCTACA CAGTGGGAAC        3780

TCGCTTCATG TTGTCAAGAA AGGGAGCTGT TTTCTGCAGA GAAGAGGAGG TAGTCCCGTC        3840

TTTTAGGGTC CTGGCCTGGG GACAGTGTTC ATTAAGGATT CAGGCTCTTT CTGTGAAGAC        3900

TGAGAGGACA CTTACCTGTG GATCC                                              3925
```

(2) INFORMATION FOR SEQ ID NO: 2:

(i) SEQUENCE CHARACTERISTICS:
       (A) LENGTH: 1593 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 1..1593

(xi) SEQUENCE DESCRIPTION: SEQ ID NO: 2:

```
ATG GAA CCC ACC GCG CCA ACC GGT CAG GCC CGG GCG GCG GCC ACC AAA         48
Met Glu Pro Thr Ala Pro Thr Gly Gln Ala Arg Ala Ala Ala Thr Lys
 1               5                  10                  15

CTG TCG GAA GCG GTG GGA GCC GCG CTA CAA GAG CCC CAG AGG CAG CGG         96
Leu Ser Glu Ala Val Gly Ala Ala Leu Gln Glu Pro Gln Arg Gln Arg
            20                  25                  30

CGC CTG GTG CTG GTC ATC GTG TGC GTT GCA CTG TTA CTG GAC AAC ATG        144
Arg Leu Val Leu Val Ile Val Cys Val Ala Leu Leu Leu Asp Asn Met
        35                  40                  45

TTG TAC ATG GTC ATC GTG CCC ATT GTT CCC GAC TAT ATC GCC CAC ATG        192
Leu Tyr Met Val Ile Val Pro Ile Val Pro Asp Tyr Ile Ala His Met
    50                  55                  60

CGC GGG GGC AGC GAG GGC CCG ACC CTG GTC TCT GAG GTG TGG GAA CCC        240
Arg Gly Gly Ser Glu Gly Pro Thr Leu Val Ser Glu Val Trp Glu Pro
65                  70                  75                  80

ACT CTG CCG CCG CCC ACT CTG GCT AAT GCC AGT GCC TAC TTG GCC AAC        288
Thr Leu Pro Pro Pro Thr Leu Ala Asn Ala Ser Ala Tyr Leu Ala Asn
                85                  90                  95

ACG TCG GCG TCC CCG ACG GCT GCC GGG TCG GCT CGG TCA ATC CTG CGA        336
Thr Ser Ala Ser Pro Thr Ala Ala Gly Ser Ala Arg Ser Ile Leu Arg
            100                 105                 110

CCT CGC TAC CCC ACA GAA AGC GAA GAT GTG AAG ATA GGT GTG CTG TTT        384
Pro Arg Tyr Pro Thr Glu Ser Glu Asp Val Lys Ile Gly Val Leu Phe
        115                 120                 125
```

```
GCC TCC AAG GCT ATC CTG CAG CTT CTG GTG AAC CCC TTA AGC GGG CCT     432
Ala Ser Lys Ala Ile Leu Gln Leu Leu Val Asn Pro Leu Ser Gly Pro
    130                 135                 140

TTC ATT GAT CGC ATG AGC TAC GAC GTG CCG CTG CTT ATA GGC CTG GGC     480
Phe Ile Asp Arg Met Ser Tyr Asp Val Pro Leu Leu Ile Gly Leu Gly
145                 150                 155                 160

GTC ATG TTC GCC TCC ACA GTC ATG TTT GCC TTT GCA GAA GAC TAT GCC     528
Val Met Phe Ala Ser Thr Val Met Phe Ala Phe Ala Glu Asp Tyr Ala
                165                 170                 175

ACG CTC TTC GCT GCG CGC AGT CTA CAA GGC CTG GGC TCG GCC TTC GCG     576
Thr Leu Phe Ala Ala Arg Ser Leu Gln Gly Leu Gly Ser Ala Phe Ala
            180                 185                 190

GAC ACG TCT GGC ATT GCC ATG ATC GCC GAC AAG TAT CCC GAG GAG CCT     624
Asp Thr Ser Gly Ile Ala Met Ile Ala Asp Lys Tyr Pro Glu Glu Pro
        195                 200                 205

GAG CGC AGT CGT GCC CTG GGC GTG GCG CTA GCC TTT ATT AGC TTT GGA     672
Glu Arg Ser Arg Ala Leu Gly Val Ala Leu Ala Phe Ile Ser Phe Gly
    210                 215                 220

AGC CTA GTG GCG CCA CCG TTT GGG GGC ATC CTC TAC GAG TTC GCG GGC     720
Ser Leu Val Ala Pro Pro Phe Gly Gly Ile Leu Tyr Glu Phe Ala Gly
225                 230                 235                 240

AAG CGT GTA CCC TTT CTA GTG CTC GCC GCT GTG TCC CTT TTC GAC GCG     768
Lys Arg Val Pro Phe Leu Val Leu Ala Ala Val Ser Leu Phe Asp Ala
                245                 250                 255

CTC CTG CTC CTG GCG GTG GCT AAG CCC TTC TCG GCT GCG GCT CGG GCG     816
Leu Leu Leu Leu Ala Val Ala Lys Pro Phe Ser Ala Ala Ala Arg Ala
            260                 265                 270

CGA GCC AAC CTG CCG GTG GGC ACA CCT ATC CAT CGC CTC ATG CTA GAC     864
Arg Ala Asn Leu Pro Val Gly Thr Pro Ile His Arg Leu Met Leu Asp
        275                 280                 285

CCT TAC ATC GCT GTG GTA GCC GGC GCG CTC ACC ACT TGT AAC ATT CCC     912
Pro Tyr Ile Ala Val Val Ala Gly Ala Leu Thr Thr Cys Asn Ile Pro
    290                 295                 300

CTT GCG TTC CTC GAG CCC ACC ATA GCC ACG TGG ATG AAG CAC ACA ATG     960
Leu Ala Phe Leu Glu Pro Thr Ile Ala Thr Trp Met Lys His Thr Met
305                 310                 315                 320

GCC GCA TCC GAG TGG GAG ATG GGC ATG GTT TGG CTG CCG GCT TTC GTG    1008
Ala Ala Ser Glu Trp Glu Met Gly Met Val Trp Leu Pro Ala Phe Val
                325                 330                 335

CCA CAC GTG TTA GGC GTC TAC CTC ACC GTG CGC CTG GCG GCG CGT TAT    1056
Pro His Val Leu Gly Val Tyr Leu Thr Val Arg Leu Ala Ala Arg Tyr
            340                 345                 350

CCA CAC CTG CAG TGG CTG TAC GGC GCT CTC GGG CTA GCG GTA ATT GGA    1104
Pro His Leu Gln Trp Leu Tyr Gly Ala Leu Gly Leu Ala Val Ile Gly
        355                 360                 365

GTG AGC TCT TGC GTC GTA CCT GCC TGT CGC TCA TTC GCG CCG TTA GTG    1152
Val Ser Ser Cys Val Val Pro Ala Cys Arg Ser Phe Ala Pro Leu Val
    370                 375                 380

GTC TCG CTC TGC GGA CTC TGC TTC GGC ATC GCG TTA GTG GAC ACA GCG    1200
Val Ser Leu Cys Gly Leu Cys Phe Gly Ile Ala Leu Val Asp Thr Ala
385                 390                 395                 400

CTC CTA CCC ACG CTC GCC TTT CTG GTG GAC GTG CGC CAC GTA TCC GTC    1248
Leu Leu Pro Thr Leu Ala Phe Leu Val Asp Val Arg His Val Ser Val
                405                 410                 415

TAT GGC AGT GTC TAT GCC ATA GCT GAC ATC TCC TAT TCT GTG GCC TAC    1296
Tyr Gly Ser Val Tyr Ala Ile Ala Asp Ile Ser Tyr Ser Val Ala Tyr
            420                 425                 430

GCG CTC GGG CCC ATA GTG GCA GGC CAC ATC GTT CAC TCT CTT GGC TTT    1344
Ala Leu Gly Pro Ile Val Ala Gly His Ile Val His Ser Leu Gly Phe
```

```
                435                 440                 445
GAG CAG CTC AGC CTG GGC ATG GGC CTG GCC AAC CTG CTC TAC GCA CCA    1392
Glu Gln Leu Ser Leu Gly Met Gly Leu Ala Asn Leu Leu Tyr Ala Pro
        450                 455                 460

GTC CTT CTT CTT TTG CGC AAT GTA GGC CTC CTT ACA CGC TCG CGT TCG    1440
Val Leu Leu Leu Leu Arg Asn Val Gly Leu Leu Thr Arg Ser Arg Ser
465                 470                 475                 480

GAG CGC GAT GTG TTG CTT GAT GAA CCG CCG CAG GGT CTG TAC GAC GCG    1488
Glu Arg Asp Val Leu Leu Asp Glu Pro Pro Gln Gly Leu Tyr Asp Ala
                485                 490                 495

GTG CGC CTG CGT GAG GTG CAG GGC AAG GAT GGC GGC GAA CCT TGT AGC    1536
Val Arg Leu Arg Glu Val Gln Gly Lys Asp Gly Gly Glu Pro Cys Ser
        500                 505                 510

CCA CCT GGC CCT TTT GAC GGG TGC GAG GAC GAC TAC AAC TAT TAC TCC    1584
Pro Pro Gly Pro Phe Asp Gly Cys Glu Asp Asp Tyr Asn Tyr Tyr Ser
            515                 520                 525

CGC AGC TAG                                                         1593
Arg Ser  *
    530
```

(2) INFORMATION FOR SEQ ID NO: 3:

(i) SEQUENCE CHARACTERISTICS:
        (A) LENGTH: 530 amino acids
        (B) TYPE: amino acid
        (D) TOPOLOGY: linear     (ii) MOLECULE TYPE: protein     (xi) SEQUENCE DESCRIPTION: SEQ ID NO: 3:

```
Met Glu Pro Thr Ala Pro Thr Gly Gln Ala Arg Ala Ala Thr Lys
 1               5                  10                  15

Leu Ser Glu Ala Val Gly Ala Ala Leu Gln Glu Pro Gln Arg Gln Arg
                20                  25                  30

Arg Leu Val Leu Val Ile Val Cys Val Ala Leu Leu Leu Asp Asn Met
                35                  40                  45

Leu Tyr Met Val Ile Val Pro Ile Val Pro Asp Tyr Ile Ala His Met
        50                  55                  60

Arg Gly Gly Ser Glu Gly Pro Thr Leu Val Ser Glu Val Trp Glu Pro
65                  70                  75                  80

Thr Leu Pro Pro Pro Thr Leu Ala Asn Ala Ser Ala Tyr Leu Ala Asn
                85                  90                  95

Thr Ser Ala Ser Pro Thr Ala Ala Gly Ser Ala Arg Ser Ile Leu Arg
                100                 105                 110

Pro Arg Tyr Pro Thr Glu Ser Glu Asp Val Lys Ile Gly Val Leu Phe
        115                 120                 125

Ala Ser Lys Ala Ile Leu Gln Leu Leu Val Asn Pro Leu Ser Gly Pro
    130                 135                 140

Phe Ile Asp Arg Met Ser Tyr Asp Val Pro Leu Leu Ile Gly Leu Gly
145                 150                 155                 160

Val Met Phe Ala Ser Thr Val Met Phe Ala Phe Ala Glu Asp Tyr Ala
                165                 170                 175

Thr Leu Phe Ala Ala Arg Ser Leu Gln Gly Leu Gly Ser Ala Phe Ala
                180                 185                 190

Asp Thr Ser Gly Ile Ala Met Ile Ala Asp Lys Tyr Pro Glu Glu Pro
            195                 200                 205

Glu Arg Ser Arg Ala Leu Gly Val Ala Leu Ala Phe Ile Ser Phe Gly
    210                 215                 220
```

```
Ser Leu Val Ala Pro Pro Phe Gly Gly Ile Leu Tyr Glu Phe Ala Gly
225                 230                 235                 240

Lys Arg Val Pro Phe Leu Val Leu Ala Ala Val Ser Leu Phe Asp Ala
            245                 250                 255

Leu Leu Leu Leu Ala Val Ala Lys Pro Phe Ser Ala Ala Arg Ala
        260                 265                 270

Arg Ala Asn Leu Pro Val Gly Thr Pro Ile His Arg Leu Met Leu Asp
        275                 280                 285

Pro Tyr Ile Ala Val Ala Gly Ala Leu Thr Thr Cys Asn Ile Pro
    290                 295                 300

Leu Ala Phe Leu Glu Pro Thr Ile Ala Thr Trp Met Lys His Thr Met
305                 310                 315                 320

Ala Ala Ser Glu Trp Glu Met Gly Met Val Trp Leu Pro Ala Phe Val
                325                 330                 335

Pro His Val Leu Gly Val Tyr Leu Thr Val Arg Leu Ala Ala Arg Tyr
                340                 345                 350

Pro His Leu Gln Trp Leu Tyr Gly Ala Leu Gly Leu Ala Val Ile Gly
                355                 360                 365

Val Ser Ser Cys Val Val Pro Ala Cys Arg Ser Phe Ala Pro Leu Val
370                 375                 380

Val Ser Leu Cys Gly Leu Cys Phe Gly Ile Ala Leu Val Asp Thr Ala
385                 390                 395                 400

Leu Leu Pro Thr Leu Ala Phe Leu Val Asp Val Arg His Val Ser Val
                405                 410                 415

Tyr Gly Ser Val Tyr Ala Ile Ala Asp Ile Ser Tyr Ser Val Ala Tyr
                420                 425                 430

Ala Leu Gly Pro Ile Val Ala Gly His Ile Val His Ser Leu Gly Phe
            435                 440                 445

Glu Gln Leu Ser Leu Gly Met Gly Leu Ala Asn Leu Leu Tyr Ala Pro
        450                 455                 460

Val Leu Leu Leu Arg Asn Val Gly Leu Leu Thr Arg Ser Arg Ser
465                 470                 475                 480

Glu Arg Asp Val Leu Leu Asp Glu Pro Pro Gln Gly Leu Tyr Asp Ala
            485                 490                 495

Val Arg Leu Arg Glu Val Gln Gly Lys Asp Gly Glu Pro Cys Ser
            500                 505                 510

Pro Pro Gly Pro Phe Asp Gly Cys Glu Asp Asp Tyr Asn Tyr Tyr Ser
        515                 520                 525

Arg Ser
    530
```

(2) INFORMATION FOR SEQ ID NO: 4:

(i) SEQUENCE CHARACTERISTICS:
        (A) LENGTH: 1902 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO: 4:

```
AAGCTTTTTG CTGAAGGCGA TCCTTCCCTG ACTGTGGCCC CATATCCTTC CGATGTAAAG        60

TCTCTGCCTT CTTATTTGGA AGCTAAAGAA TGTCATTTAG GGACCTGGAA GGAGCCAAAC       120

CCATGCCTCC CTCACTCCGA TTTTATTTGC CTAGGTGTGT GTGCCACACT GCACATGGAG       180
```

```
TGACACAGGC GTAATGAAAC ACAAGGGAAA GGGAGGTGGC ACGAAGACCT CAAAGCAGGT      240

CCCAACAGCC TGGAAACTCA ACAAGTGACC ATCTCCCTTC TCCATGCCTA GTTTCCTATG      300

GGGGTGTGTG ATGGGGTGG GGTGGATAGC ATCTACATTG TACCAAGATT GAGGAAGGAC      360

GGAGTGAGCT CACCCATGGC CCTGGCACGA ACCAGTGGG TCTGCACCTT ATCAGAGAGG      420

AACGGAGGAG CAGAGAGTTG GGTGCGAGTC CCAGAATGAA TTGGCTTCAT TCTCAGGAAG      480

CCATGGATTA TTATGTGGGC TGGAGGGCTG AGAGACAAGG TCTGCCTCTT GCTAGCACTG      540

GGAAGTTTCT TTCCTGAAAG ATTCTACTGT CCACTAACCA CCAGAAAGAA AACTGCTGCC      600

TGCGGTGTTG TCCTGCACCC TGATTTTATT CAGTCAGAGC GGCAATATAT GAATAAGTAA      660

TCACGACCAT GTAGGGCAGG AAATACCTCT TTAAAAACCA CCAGTGGGAT TTTCATAGAA      720

AAGTCAGAGG AACCCAGAGC GTTCTTAAAC TCCAGTGTCT GGAGAGCCAA GCAGGTGACA      780

GACAGAGTTC ATGAAGCAAG CTGAGGGAAA ACCCCATCGC TGGAGTGTGT GCTATGAACA      840

AAGGCACCAG GATAATATTT AAAGTTGTTT CACCGCACTT TCTGCAAGGT GGATCTTGGT      900

AATCTCTTGA TGAACAGAGG CCAAGTGGGC CAGGGTTAGT GGGGAATGTG GCTTGCCCAA      960

TGCTTTCCAT AGCCATGGCT GTCCCCATAG TTAGGCTTCC TCCCTCATTT TGAGGGCAGC     1020

TGGGCCACTG CAGGGTATGT GATGGGCAGC TCTCTACTCA GATGAGTCTG TTCCTTTCAG     1080

GAGTACCTGT GTACAGGTTG GGAGGTTGGG CACTAGACCA CTTGATTGCT GCCTCTCTCC     1140

CTGACTCTGT TCTCCATCAC CTCCTCTTGC AACTGGCTTA AGAACAGAAG CCAGCCAATT     1200

TTCCAGCTCC TTCTGTATCT TCCACCATCC CAGACAGAGT CCAGGCTCAC AATGCCTACC     1260

CAACTGAGGA AGAAATCAGA GAGTCAGGAT GCTCCCGGTG TCTGACTGCC CTTCACAAGA     1320

CCCTCATGAA CACAAGGCAG CAAGCACATG CTATAACAAC AACGGCAAAT GCTAATGATT     1380

CACACCACGC GTGTGCCACA CCCTAGTTGT ACGTACTCCT ATTCCATTTT ACAGATAAAT     1440

AAAGGGGCGG TGGGGGCAGA GGGAGGAAAC AACGGCTCCC TTGGCACTGT TATCTAGTAA     1500

GTGGCAGCAC TGGGAGCCAT CCTATCTGTC TGCATCTGGA GCTCAAATCG TGATGCCTCC     1560

TTCGGTGGAG GAAGGCTAGC TTGGGATATG GAGGCTACTG TGACTCCGGA AGACAGAGAA     1620

AAGTCCAATC TCAACAACGT CACCACTATC CCCAATCTCA GCTGACTGGC ATCCTCTCTC     1680

CTGCCAGTCT GTGGACGGGA ACGCGGGCCT CACGTGCCAT CTAGGGTCAA AACTCGTCTG     1740

AGGACACACA CTGGGCCCAA CGCAGAGGCT GATCTGTTCA GCCTGTCGGC TGCAAGCCAG     1800

GACTCTCAGC TTGTGCAGCA CCCCCGGAAG GAAGGTGAGC CTTCCTAAGC CTCTACTGAC     1860

AGCAAAGCTG CAGAGGCCCT GCCGCGTGAG ACCCAGAAGC TT                        1902

(2) INFORMATION FOR SEQ ID NO: 5:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

AATAAA                                                                   6

(2) INFORMATION FOR SEQ ID NO: 6:

(i) SEQUENCE CHARACTERISTICS:
        (A) LENGTH: 23 base pairs
```

(B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 6:

CTGTCGCTGC AAGCCAGGAC TCT                                                    23

(2) INFORMATION FOR SEQ ID NO: 7:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 7:

TGGAGGAAGA GGCAAGAGCG GA                                                     22

(2) INFORMATION FOR SEQ ID NO: 8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 8:

ACCGGTTGGC GCGGTGGGTT CCAT                                                   24

(2) INFORMATION FOR SEQ ID NO: 9:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 9:

CACCGCTTCC GACAGTTTGG TG                                                     22

(2) INFORMATION FOR SEQ ID NO: 10:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 10:

TGGGCGATAT AGTCGGGAAC AATG                                                   24

(2) INFORMATION FOR SEQ ID NO: 11:

(i) SEQUENCE CHARACTERISTICS:
            (A) LENGTH: 50 base pairs
            (B) TYPE: nucleic acid
            (C) STRANDEDNESS: single
            (D) TOPOLOGY: linear -continued (ii) MOLECULE TYPE: other nucleic acid (xi) SEQUENCE DESCRIPTION: SEQ ID NO: 11:

CTGCATCTAT CTAATGCTCC TCTCGCTACC TGCTCACTCT GCGTGACATC          50

(2) INFORMATION FOR SEQ ID NO: 12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear     (ii) MOLECULE TYPE: other nucleic acid     (xi) SEQUENCE DESCRIPTION: SEQ ID NO: 12:

GATGTCACGC AGAGTGAGCA GGTAG          25

RECOMBINANT EXPRESSION OF THE RAT VESICULAR ACETYLCHOLINE TRANSPORTER

This application was filed under 35 USC 371 as a national stage of International Application PCT/FR95/01073, filed Aug. 10, 1995, and which designated the United States.

The present invention relates to a nucleic acid sequence coding for a protein involved in the vesicular transport of acetylcholine and to the corresponding protein. It also relates to expression vectors integrating the said sequence and to the use of this sequence or the said vectors for therapeutic purposes.

Acetylcholine, ACh, is a neurotransmitter synthesized by the enzyme choline acetyltransferase, ChAT. At the ends of the cholinergic neurons, the majority of the ACh produced is transported from the cytoplasm to the inside of the synaptic vesicles. The accumulation of ACh in these vesicles is mediated by the activity of an ATPase which pumps $H^+$ ions, generating an electrochemical gradient (Anderson D. C. et al., (1982) Biochemistry 21, 3037–3043). This gradient is utilized by a transporter to take up ACh via an exchange of protons (Parsons S. M. et al., (1993), Int. Rev. neurobiol. 35, 279–390). This type of mechanism is comparable to the one involved in the transport of biogenic amines into the synaptic vesicles.

An understanding of the different mechanisms of regulation participating in the expression of ACh would be especially valuable from a therapeutic standpoint.

Recently, cDNAs coding for vesicular ACh transporters in Caenohabditis elegans and Torpedo have been cloned and sequenced (Alfonso A. et al., (1993) Science 261, 617–619; Varoqui H. et al., FEBS Letters 342, 97–102). A study of the sequences of the corresponding proteins revealed the existence of structural similarities between these two proteins, and likewise with respect to two vesicular transporters of biogenic amines in mammals, VMAT1 and VMAT2 (Liu et al., (1992) Cell 70, 539–551). These common structural features are, in particular, (i) 12 transmembrane domains (TM), (ii) the presence in these transmembrane domains of charged amino acid residues which probably participate in the transport of substrate, (iii) a glycosylated loop localized between TM1 and TM2, and (iv) cytoplasmic C- and N-terminal ends which display fewer similarities than the remainder of the protein.

The subject of the present invention is, more especially, the isolation, sequencing and characterization of a region of the gene coding for ChAT capable of expressing a vesicular ACh transporter, as well as the identification of promoter sequences involved in the expression of this transporter. It also describes cassettes for expression of this gene, vectors containing it and their use for directing the expression of this transporter.

More specifically, the present invention relates to a nucleic acid sequence coding for a protein involved in the vesicular transport of ACh, characterized in that it is localized within the first intron of the gene coding for ChAT, in the same transcriptional orientation.

From the 5' region of the gene coding for rat ChAT, and more precisely from a restriction map of this region, the inventors isolated a HindIII-BamHI fragment carrying the first intron of this gene and, in part, the sequences of the first two corresponding R and N exons, respectively, at the 5' and 3' ends of this fragment. Unexpectedly, the cloning and sequencing of this fragment revealed the presence of a 1590-bp open reading frame coding for a protein of the order of 530 amino acids, equivalent to a mass of the order of 56.5 kDa, and displaying similarities in respect of its sequence with proteins of the transporter type. This protein was identified as a rat vesicular ACh transporter and is designated hereinafter rVAT.

This DNA sequence is, more specifically, localized within the first intron of the gene coding for ChAT, downstream of the R-type promoter of the ChAT gene and in the same transcription orientation as the ChAT gene. It is not interrupted by any intron.

More especially, the present invention relates to a nucleic acid sequence coding for a vesicular ACh transporter, characterized in that it comprises all or part of SEQ ID No. 1 or one of its derivatives.

Preferably, the sequence comprises all or part of the sequence SEQ ID No.2 or one of its derivatives.

For the purposes of the present invention, the term derivative denotes any sequence differing from the sequence under consideration as a result of the degeneracy of the genetic code, obtained by one or more modifications of a genetic and/or chemical nature, as well as any sequence hybridizing with these sequences or fragments of the latter and whose product possesses the stated activity. Modification of a genetic and/or chemical nature may be understood to mean any mutation, substitution, deletion, addition and/or modification of one or more residues. Such derivatives may be generated for different purposes, such as, in particular, that of increasing the affinity-of the corresponding polypeptide for its ligand(s), that of improving its levels of production, that of increasing its resistance to proteases, that of increasing and/or modifying its activity or that of endowing it with new pharmacokinetic and/or biological properties. Among derivatives resulting from an addition, chimeric nucleic acid sequences containing an additional heterologous portion linked to one end may, for example, be mentioned. The term derivative also comprises sequences homologous to the sequence under consideration, originating from other cellular sources, and in particular from cells of human origin, or from other organisms, and possessing an activity of the same type. Such homologous sequences may be obtained by hybridization experiments. The hybridizations may be carried out using nucleic acid libraries, employing as probe the native sequence or a fragment of the latter, under conventional stringency conditions (Maniatis et al., see general techniques of molecular biology), or preferably under high stringency conditions.

The present invention shall also be understood to cover the corresponding antisense sequences whose expression enables transcription of cellular mRNAs to be controlled. Such sequences can consist of all or part of the nucleic acid sequence under consideration, transcribed in the reverse orientation.

More preferably, the sequence in question is the nucleic acid sequence coding for the rat vesicular ACh transporter, rVAT.

Bearing in mind the localization of the gene according to the invention, namely in the first intron of the gene coding for ChAT, downstream of the R-type ChAT promoter and in the same transcriptional orientation, the inventors sought to find out whether the ChAT and VAT mRNAs could be expressed from the same promoter.

This hypothesis was verified experimentally. Two forms of mRNA coding for the VAT transporter were identified. They contain all or part of the sequence of the R1- or R2-type R exon (of ChAT mRNA) (Kengaku et al. Mol. Brain Res. 18: 71–76 (1993)) (FIG. 1), immediately followed by the sequence of a second exon beginning 308 bp upstream of the translation initiation codon (of VAT). Besides these two mRNAs, there are three other forms of VAT mRNA which are apparently more abundant than the two forms mentioned above, coding for the polypeptide which is the subject of the invention. One form of VAT mRNA contains all or part of the R exon mentioned above. The 5' ends of the other two forms are localized downstream of the R exon. The form which we designate V1, of approximately 2.6 kb, has two 5' ends located 426 bp and 402 bp upstream of the translation initiation codon of VAT (positions 949 and 972, respectively, on SEQ ID No. 1). The form of VAT mRNA which we designate V2, of approximately 3 kb, has several 5' ends located between 863 bp and 888 bp upstream of the translation initiation codon of VAT (positions 486 to 511 of SEQ ID No. 1).

The subject of the present invention is also promoter regions involved in the expression of VAT and localized in the gene coding for ChAT. Such regions are, more especially, the promoter region comprising all or part of SEQ ID No.4 or one of its derivatives, and attached promoter regions localized in SEQ ID No. 1.

For the purposes of the present invention, promoter region denotes the sequence or sequences responsible for the expression of VAT. This applies especially to promoter, activation and regulatory sequences and/or sequences permitting a tissue-specific expression.

SEQ ID No.4 is already known to control the expression of the ChAT gene (Bejanin et al., J. Neurochem.58: 1580–1583 (1992)). Unexpectedly, this region proved also to be responsible for the expression of the gene coding for VAT, and more specifically for at least two types of VAT mRNA. It was thus demonstrated that VAT and ChAT mRNAs may be produced from the same R-type ChAT promoter. Furthermore, two promoter regions responsible for the production of V1- and V2-type VAT mRNAs have been identified downstream of the R exon in the first intron of the ChAT gene. V1-type VAT mRNA is produced from a promoter located between positions 584 and 1027 of SEQ ID No. 1, whereas V2-type mRNA is produced from a promoter lying between positions 2 and 583 of the sequence SEQ-ID No. 1.

The subject of the present invention is also the use of these promoter regions to control and/or participate in the expression of genes. These promoter regions are also advantageous for targeting the expression of a protein in cholinergic neurons. Naturally, these promoter regions are especially useful for directing the expression of a vesicular acetylcholine transport protein, the expression being coupled, where appropriate, with that of another gene.

The invention relates, in addition, to a polypeptide involved in the vesicular transport of ACh, capable of being expressed by a nucleic acid sequence as described above.

The polypeptides of the invention may be obtained by expression in a cell host of a nucleotide sequence as described above, by chemical synthesis, on the basis of the sequence SEQ ID No. 2 using techniques known to a person skilled in the art, or by a combination of these techniques.

Comparison of this protein SEQ ID No. 3 with proteins already known as an ACh transporter, such as those of Torpedo or Caenorhabditis elegans, has enabled some similarities to be demonstrated. Thus, the protein according to the invention possesses approximately 77% homology with the Torpedo protein and 56% homology with the Caenorhabditis elegans protein, out of 352 amino acids.

In the case of the abovementioned significant homologies, it is noted especially that the 12 transmembrane domains, (TM), representing the already known transporters, exist in the protein according to the invention. In particular, the aspartic acid residues of transmembrane domains 1, 6, 10 and 11 and the lysine residue of transmembrane domain 2, which probably participate in the binding with the substrate, are present. The considerable disparity between the protein according to the invention and other known transporters occurs in the highly hydrophilic loop located between the first two transmembrane domains and the N- and C-terminal ends. In the case of the present invention, the loop integrates two potential N-glycosylation sites.

These observations collectively demonstrate that the claimed protein belongs to the family of vesicular neurotransmitter transporters containing 12 transmembrane domains.

More specifically, it is a protein which comprises all or part of SEQ ID NO: 3 or a derivative thereof. For the definition of the term derivative, reference may be made to the definition put forward above.

More preferably, it is the rat vesicular ACh transporter, hereinafter designated rVAT.

Preferably, the nucleic acid sequences according to the invention form part of a vector. The use of such a vector makes it possible, in effect, to improve the administration of the nucleic acid in the cells to be treated, and also to increase its stability in the said cells, thereby enabling a lasting therapeutic effect to be obtained.

The vector used may be of various origins, provided it is capable of transforming animal cells, preferably human nerve cells. In a preferred embodiment of the invention, a viral vector is used, which may be chosen from adenoviruses, retroviruses, adeno-associated viruses (AAV), herpesvirus, cytomegalovirus (CMV), vaccinia virus, and the like. Vectors derived from adenoviruses, from retroviruses or from AAV incorporating heterologous nucleic acid sequences have been described in the literature [Akli et al., Nature Genetics 3 (1993) 224; Stratford-Perricaudet et al., Human Gene Therapy 1 (1990) 241; EP 185 573, Levrero et al., Gene 101 (1991) 195; Le Gal la Salle et al., Science 259 (1993) 988; Roemer and Friedmann, Eur. J. Biochem. 208 (1992) 211; Dobson et al., Neuron 5 (1990) 353; Chiocca et al., New Biol. 2 (1990) 739; Miyanohara et al., New Biol. 4 (1992) 238; WO91/18088].

Hence the present invention also relates to any recombinant virus comprising, inserted into its genome, a nucleic acid sequence as defined above.

Advantageously, the recombinant virus according to the invention is a defective virus. The term "defective virus" denotes a virus incapable of replication in the target cell. Generally, the genome of the defective viruses used in the context of the present invention hence lacks at least the sequences needed for replication of the said virus in the infected cell. These regions may be either removed (wholly or partially), or rendered non-functional, or substituted by other sequences, and in particular by the nucleic acid of the invention. Preferably, the defective virus nevertheless retains the sequences of its genome which are needed for encapsidation of the viral particles.

It is especially advantageous to use the nucleic acid sequences of the invention in a form incorporated in a defective recombinant adenovirus, AAV or retrovirus.

As regards adenoviruses, there are different serotypes of these, whose structure and properties vary somewhat but which are not pathogenic for man, and in particular non-immunosuppressed subjects. Moreover, these viruses do not integrate in the genome of the cells they infect, and can incorporate large fragments of exogenous DNA. Among the different serotypes, it is preferable to use, in the context of the present invention, adenoviruses type 2 or 5 (Ad 2 or Ad 5). In the case of Ad 5 adenoviruses, the sequences needed for replication are the E1A and E1B regions.

The defective recombinant viruses of the invention may be prepared by homologous recombination between a defective virus and a plasmid carrying, inter alia, the nucleotide sequence as defined above (Levrero et al., Gene 101 (1991) 195; Graham, EMBO J. 3(12) (1984) 2917). Homologous recombination takes place after cotransfection of the said virus and said plasmid in a suitable cell line. The cell line used should preferably (i) be transformable by the said elements, and (ii) contain the sequences capable of complementing the portion of the genome of the defective virus, preferably in integrated form in order to avoid risks of recombination. As an example of a line which can be used for the preparation of defective recombinant adenoviruses, there may be mentioned the human embryonic kidney line 293 (Graham et al., J. Gen. Virol. 36 (1977) 59) which contains, in particular, integrated in its genome, the left-hand portion of the genome of an Ad5 adenovirus (12%). As an example of a line which can be used for the preparation of defective recombinant retroviruses, the CRIP line (Danos and Mulligan, PNAS 85 (1988) 6460) may be mentioned.

Thereafter, the viruses which have multiplied are recovered and purified according to standard techniques of molecular biology.

The subject of the present invention is also a pharmaceutical composition comprising at least one nucleotide sequence, vector or polypeptide according to the invention.

It also relates to any use of a sequence or vector as are claimed for the preparation of a pharmaceutical composition intended for the treatment of pathologies affecting the nervous system.

The nucleic acid sequence, as claimed, coding for an acetylcholine transporter is, in addition, most especially useful for screening new biologically active products, and especially those involved in the expression and/or regulation of-acetylcholine.

The subject of the present invention is also transgenic animals into the genome of which at least one nucleic acid sequence, as claimed, coding for an acetylcholine transporter is inserted.

The examples and figures presented below by way of illustration and without implied limitation bring out other advantages and features of the present invention.

BRIEF DESCRIPTION OF THE DRAWINGS

FIG. 1: Diagrammatic representation of the 5' region of the rat ChAT gene and of the different ChAT mRNAs The clear and black boxes indicate, respectively, the coding and non-coding exons. R, N and M are the 3 non-coding ChAT exons. The 1590-bp open reading frame identified from the sequencing of a 3940-bp HindIII(H)-BamHI(B) gene fragment, is also shown. The potential translation initiation codon, ATG (position +1), is flanked by a cytosine (position −1) and two guanosine residues (positions −3 and +4), which tally with the consensus sequence of Kozak (Kozak M. J., Cell. Biol. 115, 887–903 1991). It is preceded by a stop codon in frame located 726 bp upstream. The open reading frame is followed by consensus polyadenylation sequences. The most probable one, designated PA (AATAAA) (SEQ ID No. 5), is located 389 bp downstream of the termination codon.

Lane 1: Spinal cord poly(A)$^+$ RNA (1 µg);
Lanes 2–11: 10 µg of:
   2,3: spinal cord RNA (2 different preparations);
   4: brain stem RNA;
   5: adrenal gland poly(A)$^+$ RNA;
   6: olfactory bulb RNA;
   7: cerebellum RNA;
   8: liver RNA;
   9: spinal cord RNA;
   10: septal region poly(A)$^+$ RNA;
   11: striatum poly(A)$^+$ RNA.

The RNA blots are prepared in the presence of RNA molecular weight markers (Gibco BRL). Lanes 1 to 8 and 9 to 11 represent the results of two independent experiments. The autoradiographs are exposed for three days at a temperature of −70° C. with an intensifying screen.

FIG. 3: Diversity of the rVAT mRNAs in rat spinal cord The figure shows the results of Southern blot analysis of the cDNA amplification products (lanes 1,2) and of the SLIC products (lanes 3,4). The clear and black boxes indicate, respectively, the non-coding and coding exons. The oligonucleotides used for the synthesis of cDNA (P), for the amplification (two sense primers 1,2 upstream and a common antisense primer L) and for the Southern hybridization (H) are indicated diagrammatically by arrows. The poly(A)$^+$ RNA is subjected to a synthesis of the first strand of cDNA with or, as a control, without reverse transcriptase. The amplifications of the cDNA (+) or the controls (−) with the pair of oligonucleotides L and 1 or 2 are shown, respectively, in lanes 1 and 2. The amplifications with oligonucleotides L and A5'l of the CDNA (+) or the controls (−), ligated or otherwise, are seen, respectively, in lanes 3 and 4. The vertical bars in the exons R and rVAT represent the splicing sites deduced from the sequences of the two DNA fragments obtained in lane 1. The 5' splicing site in the R exon corresponds to the one shown in FIG. 1. The consensus sequence of the 3' splicing site is underlined. The position of the nucleotide located nearest the 5' end for the SLIC products sequenced is indicated by an asterisk.

EXAMPLES

Example 1

Synthesis of the First Strand of cDNA (primer extension) and Ligation of an Oligonucleotide to the Single-stranded cDNA (SLIC)

Figure 3:
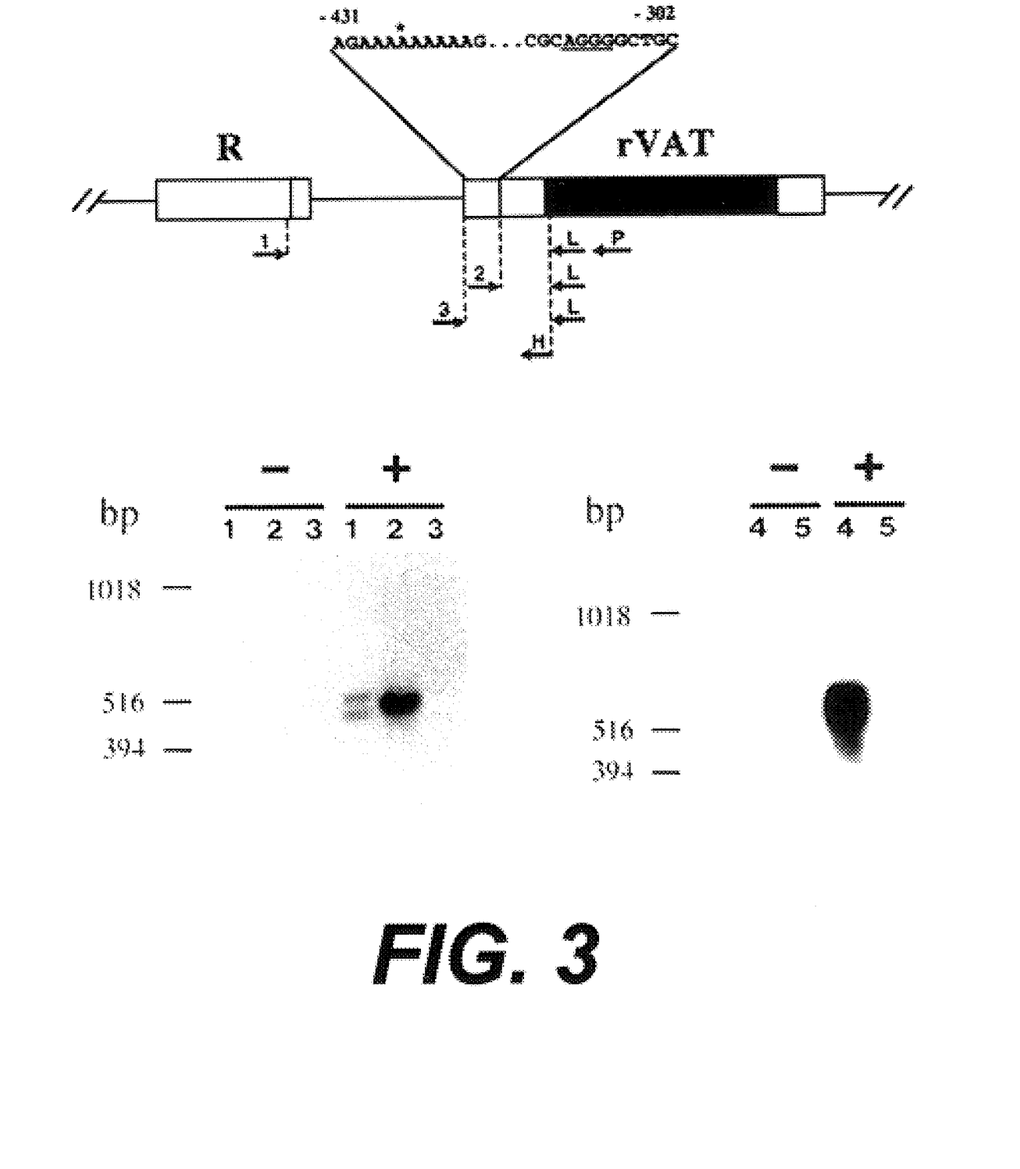

The RNA is extracted from rat spinal cord using the RNAzol method (Bioprobe system). The poly(A)$^+$ RNA is purified using Dynabeads® kit (Dynal). The first strand of cDNA is synthesized from 1 µg of poly(A)$^+$ RNA in a reverse transcription buffer in the presence of 100 µg/ml BSA, 15 units of RNasin (Promega), 14 mM β-mercaptoethanol, 1 mM dNTPs, 4 mM pyrophosphate, 7.5 pM primer oligonucleotide P (FIG. 3) and 40 units of reverse transcriptase (RTase, Promega). The reaction mixture is incubated for 45 minutes at 42° C. A control is performed in the absence of RTAse. cDNA and controls are heated for 5 minutes at 95° C. in order to denature the DNA-RNA heteroduplexes, and then purified with the Prep-A-Gene® Kit (Biorad). In the SLIC experiments, a 50-mer oligonucleotide (A5'NV) is ligated to the 3' end of the first strand of purified cDNA using T4 RNA ligase (Boehringer) as described in the literature (Dumas et al., Nucleic Acids Res. 19 5227–5232, 1991). A control is performed in the absence of the enzyme. The ligation products and controls are then purified using the Prep-A-Gene® Kit.

Example 2
Amplification Experiments

Figure 1:
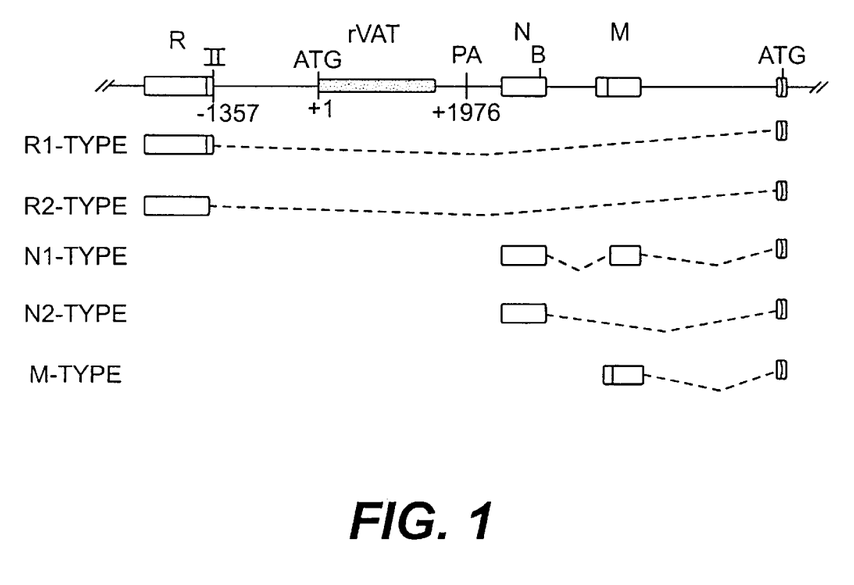
Figure 2:
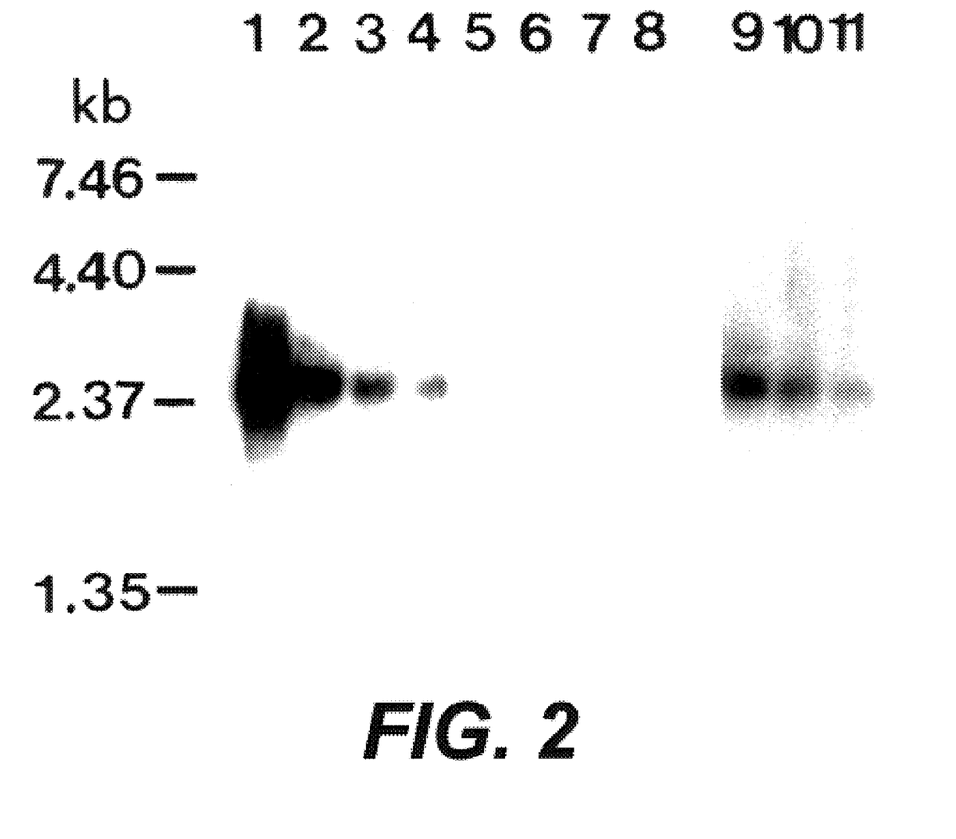
FIG. 2: Analysis by the Northern technique of the distribution of rVAT mRNAs in different rat tissues with a probe specific for the open reading frame (position 31–1724 as defined in FIG. 1)

The cDNAs and the SLIC products are amplified in a Techne Thermal Cycler® (30 or 40 amplification cycles, respectively). Each cycle consists of: 45s at 94° C., 45s at 65° C. and 50s at 72° C. The sense primers used are the following: oligonucleotides 1 or 2 for the cDNAs and the oligonucleotide A5'1 (complementary to a portion of A5'NV) for the cDNAs ligated at the 3' end. A common antisense primer L is used. The amplification products are separated on 2% agarose gel and analysed by the Southern blotting technique using the oligonucleotide H as probe. The portions of the gel containing the bands observed are isolated, and the DNA they contain is purified, subdloned into plasmid pUC19 (Appligene) and sequenced on both strands by means of the Sequenase® kit (USB, Amersham). The sequences and the positions (see FIG. 1) of the oligonucleotides used are:

1 (−1486, 5'-CTGTCGCTGCAAGCCAGGACTCT-3') (SEQ ID No. 6)

2 (−410, 5'-TGGAGGAAGAGGCAAGAGCGGA-3') (SEQ ID No. 7)

H (+24, 5'-ACCGGTTGGCGCGGTGGGTTCCAT-3') (SEQ ID No. 8)

L (+62, 5'-CACCGCTTCCGACAGTTTGGTG-3') (SEQ ID No. 9)

P (+187, 5'-TGGGCGATATAGTCGGGAACAATG-3') (SEQ ID No. 10)

A5'NV (5'-CTGCATCTATCTAATGCTCCTCTCGCTACCTGCTCACTCTGCGTGACATC-3') (SEQ ID No. 11)

A5'1 (5'-GATGTCACGCAGAGTGAGCAGGTAG-3') (SEQ ID No. 12)

Example 3
Analysis of the RNA

The RNAs or poly(A)$^+$ RNAs are prepared from rat tissues as described above, fractionated on agarose gel (1%)/formaldehyde and transferred onto nylon membranes (Hybond N$^+$, Amersham) as described in the literature (Faucon Biguet et al., EMBO J., 5 287–291 1986). The filters are hybridized at 42° C., in a buffer containing 50% (vol/vol) of formamide, with an. SmaI-EcoRI fragment (position 31–1724) labelled by random priming (19) with [α-$^{32}$P]dCTP (3000 Ci/mmol; Amersham) and having a specific activity of $1.2 \times 10^9$ cpm/μg. The final washes of the filters are performed at 65° C. in 0.1×SSC/0.1% SDS solution.

Abbreviations used:

ChAT: choline acetyltransferase

ACh: acetylcholine

VMAT: vesicular monoamine transporter

TM: transmembrane domain rVAT: rat vesicular acetylcholine transporter

SLIC: ligation of single-stranded cDNA

---

What is claimed is:

1. A recombinant viral vector comprising a nucleic acid sequence encoding a rat vesicular acetylcholine transport protein, wherein said nucleic acid sequence comprises a sequence as set forth in SEQ ID NO: 1.

2. The recombinant viral vector according to claim 1, wherein said vector is derived from a virus selected from the group consisting of adenovirus, retrovirus, adeno-associated virus, herpesvirus, cytomegalovirus, and vaccinia virus.

3. The recombinant viral vector according to claim 1, wherein said viral vector is replication defective.

4. A composition comprising one or more vectors according to claim 1.

5. A method for expressing a vesicular acetylcholine transport protein in a cultured cell comprising administration to the cell of the recombinant viral vector according to claim 1 and culturing the cell under conditions that result in the expression of the vesicular acetylcholine transport protein.

6. A method for directing expression of a gene encoding a rat vesicular acetylcholine transport protein in a cultured cell comprising     1) operably linking said gene to a promoter region selected from the group consisting of a region lying between positions 2 and 583 of Seq ID No: 1, and a promoter region comprising SEQ ID No: 4;

2) administering the gene operably linked to a promoter region as formed in step 1) to the cell; and     3) culturing the cell under conditions that result in the expression of the vesicular acetylcholine transport protein.

\* \* \* \* \*